(12) United States Patent
Alaoui Ismaili et al.

(10) Patent No.: US 7,807,204 B2
(45) Date of Patent: Oct. 5, 2010

(54) **PROCESSES FOR PRODUCTION OF *HOODIA* PLANT EXTRACTS CONTAINING STEROIDAL GLYCOSIDES**

(75) Inventors: Smail Alaoui Ismaili, Barcelona (ES); Sybille Buchwald-Werner, Monheim am Rhein (DE); Frederik Michiel Meeuse, Vlaardingen (NL); Kevin John Povey, Purfleet (GB)

(73) Assignee: Phytopharm PLC, Godmanchester, Cambrige (GB)

( * ) Notice: Subject to any disclaimer, the term of this patent is extended or adjusted under 35 U.S.C. 154(b) by 499 days.

(21) Appl. No.: 11/893,059

(22) Filed: Aug. 14, 2007

(65) Prior Publication Data
US 2008/0044552 A1 Feb. 21, 2008

(30) Foreign Application Priority Data
Aug. 17, 2006 (EP) .................................. 06119076

(51) Int. Cl.
*A61K 36/33* (2006.01)
*A61K 36/00* (2006.01)

(52) U.S. Cl. ....................................... 424/767; 424/725
(58) Field of Classification Search ........................ None
See application file for complete search history.

(56) References Cited

U.S. PATENT DOCUMENTS

| 6,376,657 | B1 | 4/2002 | Van heerden et al. ............ 536/5 |
| 7,008,648 | B2 | 3/2006 | Corley et al. ................. 424/725 |
| 7,033,616 | B2 * | 4/2006 | Rubin et al. ................. 424/725 |
| 7,060,308 | B2 | 6/2006 | Rajendran et al. ............ 424/725 |
| 7,166,611 | B2 * | 1/2007 | Van Heerden et al. ........ 514/278 |
| 7,265,101 | B2 * | 9/2007 | Raskin et al. ................. 514/170 |
| 7,501,135 | B2 * | 3/2009 | Hakkinen et al. ............ 424/725 |
| 2007/0104805 | A1 * | 5/2007 | Udell ......................... 424/725 |
| 2008/0003268 | A1 * | 1/2008 | Abrahamse et al. .......... 424/439 |
| 2009/0263510 | A1 * | 10/2009 | Povey et al. ................. 424/725 |
| 2009/0264376 | A1 * | 10/2009 | Batenburg et al. ............ 514/26 |
| 2010/0056767 | A1 * | 3/2010 | Gunning et al. ................. 536/5 |

FOREIGN PATENT DOCUMENTS

| FR | 2 854 075 | 10/2004 |
| GB | 875 760 | 8/1961 |
| WO | 98/46243 | 10/1998 |
| WO | 2005/099737 | 10/2005 |
| WO | 2005/116049 | 12/2005 |

OTHER PUBLICATIONS

PCT International Search Report in a PCT application PCT/EP2007/057320.
EP Search Report in an EP application EP 06 11 9076.
Abstract of FR 2 854 075 published Oct. 29, 2004.
Abstract of SU 168 9394 published Nov. 7, 1991.
Cui et al., "Removal of Trace Heavy metals from a Natural Medicine Material by Supercritical CO2 Chelating Extraction", Industrial and Engineering Chemical Research, vol. 40, No. 16, 2001, pp. 3659-3663.

* cited by examiner

*Primary Examiner*—Christopher R. Tate
(74) *Attorney, Agent, or Firm*—Harness, Dickey & Pierce, P.L.C.; J. Timothy Keane; Kisuk Lee

(57) ABSTRACT

Processes for the production of *Hoodia* plant extracts with a high content of steroidal glycosides and for minimizing heavy metal and/or polyaromatic hydrocarbon content in *Hoodia* extracts.

16 Claims, No Drawings

PROCESSES FOR PRODUCTION OF *HOODIA* PLANT EXTRACTS CONTAINING STEROIDAL GLYCOSIDES

TECHNICAL FIELD

The present invention relates to processes for producing *Hoodia* plant extracts.

BACKGROUND OF THE INVENTION

Extracts obtainable from plants of the *Asclepiadaceae* family, particularly the *Hoodia* genus (formerly the *Hoodia* and *Trichocaulon* genera) have been shown to have an appetite suppressant activity. U.S. Pat. No. 6,376,657 discloses that these plants contain steroidal glycosides having the formula 1:

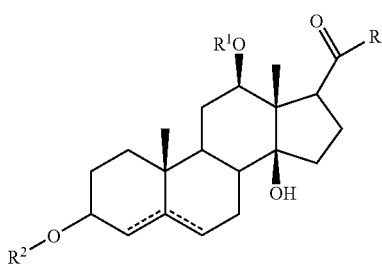

wherein

R=alkyl;

R$^1$=H, alkyl, tiglyol, benzoyl or any other organic ester group;

R$^2$=H or one or more 6-deoxy carbohydrates, or one or more 2,6-dideoxy carbohydrates, or glucose radical or combinations thereof; and wherein the broken lines indicate the optional presence of a further bond between carbon atoms C4 and C5 or between carbon atoms C5 and C6.

U.S. Pat. No. 6,376,657 also discloses processes to extract steroidal glycosides having the formula 1 from *Hoodia* plants, involving treating plant material with a solvent to extract a fraction having appetite suppressant activity, separating the extraction solution from the rest of the plant material, removing the solvent from the extraction solution, optionally treating the solution with the additional solvent, and recovering the extract. The solvents specifically disclosed include methylene chloride, also known as dichloromethane. The patent also discloses methods for synthesizing various steroidal glycosides.

U.S. Pat. No. 7,060,308 (Rajendran et al.) discloses *Caralluma* extracts. U.S. Pat. No. 7,008,648 (Corley et al.) discloses extracts obtainable from plants of the *Stapelia* and *Orbea* genera. WO 2005/099737 (Rutgers University) also discloses extracts and processes of obtaining extracts from *Asclepias* plants.

WO2005/116049 (Unilever) discloses that steroidal glycosides can be extracted or separated from undesirable components present in plant material of the *Asclepiadaceae* family by means of liquid or supercritical carbon dioxide.

The need remains for alternate processes of preparing *Hoodia* extracts, resulting in a high content of steroidal glycosides and suitable for use in foods (e.g. the use of chlorinated solvents is undesirable).

Depending on the origin of the plant materials, they may contain traces of heavy metals like copper or zinc and polyaromatic hydrocarbons (PAH) which may be enriched during the extraction processes. Thus, there is also a need for processes which attain extracts with minimised heavy metal and PAH content.

Therefore, the object of the present invention is to develop a manufacturing process for obtaining a *Hoodia* plant extract with a high content of steroidal glycosides and which uses food grade solvents.

Yet another object of the present invention is to obtain by-products like water-soluble short-chain active principles, long-chain waxes and fatty acids from *Hoodia* plants in a purity which allows using them for other purposes in order to make the process even more economic.

Still another object of the invention is to develop a manufacturing process for obtaining *Hoodia* extracts with minimised heavy metal and/or PAH content.

DEFINITION OF THE INVENTION

The above and other objects are attained by the present invention which includes, in its first aspect, a process for obtaining a *Hoodia* plant extract comprising steroidal glycosides, the process comprising the steps of:

(a) extracting *Hoodia* plants with aqueous $C_1$-$C_3$ aliphatic alcohols to provide a water-insoluble waste residue and a first aqueous extract E1;

(b) subjecting the first extract E1 to at least one liquid-liquid extraction with lower paraffin hydrocarbons to provide an organic phase A1 and a second aqueous extract E2;

(c) subjecting the second extract E2 to at least one liquid-liquid extraction with an aqueous mixture of lower paraffin hydrocarbons and lower dialkyl ketones to provide at least one aqueous phase A2 and at least one organic extract E3; and (d) drying the organic extract E3 to the desired dry matter content to provide the *Hoodia* plant extract comprising steroidal glycosides.

The process according to the present invention includes a defined cascade of liquid-liquid extractions using defined organic solvents, which allows to achieve *Hoodia* extracts exhibiting a total content of steroidal glycosides—calculated on the dried final product—of more than 35 and typically more than 70% by weight. The well-balanced cascade of solvents avoids the use of non-food grade materials; therefore, the extracts obtainable according to the present invention comply with the regulatory conditions for use in food. An additional benefit is generated from the fact that the process delivers organic and aqueous side fractions comprising interesting molecules like short-chain actives, long-chain waxes or fatty acids also in high yields and good quality, which can be used for other purposes, e.g. in cosmetic applications, which adds additional value to the process and makes it even more economic.

In its second aspect, the invention includes a process for obtaining a *Hoodia* plant extract comprising steroidal glycosides, the process comprising the steps of:

(a) extracting *Hoodia* plants, to obtain an extract (b) treating the extract with a treatment selected from the group consisting of absorbents (e.g. activated charcoal to adsorb PAH), chelating agents (e.g., EDTA or citric acid) and mixtures thereof, to obtain a purified extract;

(c) drying the purified extract to the desired dry matter content to provide the *Hoodia* plant extract comprising steroidal glycosides.

In yet another aspect, the invention includes *Hoodia* plant extracts obtainable by these processes, and food products incorporating such extracts.

DETAILED DESCRIPTION OF THE INVENTION

Except in the operating and comparative examples, or where otherwise explicitly indicated, all numbers in this description indicating amounts of material or conditions of reaction, physical properties of materials and/or use are to be understood as modified by the word "about."

It should be noted that in specifying any range of concentration or amount, any particular upper concentration can be associated with any particular lower concentration or amount.

For the avoidance of doubt the word "comprising" is intended to mean "including" but not necessarily "consisting of" or "composed of." In other words, the listed steps or options need not be exhaustive.

"Steroidal glycoside" as used herein means a steroid (four fused rings), further comprising at least one side group substitution which is a glycoside (a molecule in which a sugar group is bonded through its anomeric carbon to another group via an O-glycosidic bond), preferably a deoxy or di-deoxy glycoside and includes all steroidal glycosides eluting after 15 minutes as described in HPLC Steroidal Glycoside Analysis hereinbelow.

Step a—Pre-Extraction

Step (a) of the inventive process produces a first liquid extract E1 from *Hoodia* plants. The plants suitable as starting materials are those of *Hoodia* genus. Suitable plants include but are not limited to *Trichocaulon piliferum, Trichocaulon officinale, Hoodia currorii, Hoodia gordonii, Hoodia lugardii* and mixtures thereof.

The plants are extracted with aqueous $C_1$-$C_3$ aliphatic alcohols, more particularly aqueous methanol, ethanol, n-propanol, or isopropylalcohol or their mixtures. Higher aliphatic alcohols like, e.g., butanol are less preferred due to their lower polarity. The water content of the alcohols can range between 1 and 25, preferably 2 and 15, and particularly between 5 and 15% w/w. The preferred solvent, however, is methanol comprising 10% water. The amount of methanol used for the extraction can be chosen easily by the skilled person and should be sufficient to effect an extraction, which is preferably carried out in a percolator. The maximum extraction temperature is limited by the boiling point of the solvents (which depends on the pressure); extraction below boiling point is also possible. Typically step (a) is conducted at a temperature of 50 to 80° C., and preferably at about 60-70° C.

The plants are preferably first dried, in order to reduce the bulk of the plants to be extracted. If dried then generally to a moisture content of less than 12%, preferably less than 5%.

The dried plant material is preferably cut, preferably into pieces of 2×2×2 mm, most preferably smaller then 1×1×1 mm. A typical ratio would be 1 part of dried plant material and 3 to 15 parts of solvent.

The whole plants may be used, but, preferably, to reduce potential microbial contamination, the roots are cut off and the plants are used without roots.

Once the extraction has been completed, the aqueous/alcoholic phase is preferably subjected to a filtration to remove the depleted plant material, which is still useful as fuel for generating heat to dry the starting material. In a further preferred embodiment, the filtrate is concentrated by evaporation of all or part of the solvent to give the first extract E1, which shows a water content of typically 20 to 40% by weight after the removal of the alcohol. The alcohol which is separated from the extract can be recycled.

Step b—Separation of Organic By-Products

Step (b) is directed to the removal of unwanted organic by-products like long-chain waxes and fatty acids. Therefore, the aqueous extract E1 is subjected to a liquid-liquid extraction with lower paraffin hydrocarbons. Suitable lower paraffin hydrocarbons include but are not limited to n-pentane, n-hexane, n-heptane. Preferably, n-hexane, n-heptane or their mixtures are employed. This step is typically conducted at a temperature of 20 to 70° C., preferably between 40° C. and 70° C. After the phases have separated, the upper organic layer A1 comprising said organic by-products can be removed, while the desired steroidal glycosides remain in the aqueous extract E2. The organic phase may optionally be subjected to further purification, especially for separating the waxes from the fatty acids, both useful e.g. as consistency factors or stabilisers for cosmetic applications. The aqueous phase is preferably concentrated to give a second extract E2 with a water content of 40 to 70% by weight of the aqueous phase.

Step c—Extraction of the Steroidal Glycosides

The aqueous extract E2 comprises the various (longer) steroidal glycosides along with some other molecules which are not desired for the intended purpose. Therefore, in step (c) the desired steroidal glycosides are separated from the other molecules by means of another liquid-liquid extraction, which is conducted with an aqueous mixture of lower paraffin hydrocarbons and lower dialkyl ketones. Suitable lower paraffin hydrocarbons have been described above.

Suitable lower dialkyl ketones include but are not limited to methylethyl ketone (ethylmethyl ketone). Preferably, step (c) is conducted with an aqueous mixture of (1) n-hexane and/or n-heptane and (2) acetone and/or methylethyl ketone (MEK). The preferred solvent, however, is a mixture of n-heptane and MEK. The weight ratio between the solvents (1) and (2) is not critical since it works over a broad range. Preferred ranges, however, are 25:75 to 75:25, and in particular 40:60 to 60:40 to get optimum partitioning between organic and water phase. The extraction is conducted in the presence of water, which stems in one part from the aqueous phase which is subjected to said extraction and in the other part from water which is added to the process. The total amount of water must be sufficient to achieve a separation of the organic and the aqueous phase, and will usually lie in a range of 20 to 80% by weight, calculated on the weight of the organic solvent. The extraction can be carried out at room temperature; however, typically it is conducted between 20 and 50° C.

Step (c) extraction results in separation of the phases and an aqueous Phase A2 comprising all short-chain molecules is obtained as well as an organic phase E3 comprising the desired steroidal glycosides. Since the plants may comprise a number of different steroidal glycosides, one extraction may not be enough to convert the total amount of the steroidal glycosides into the organic phase E3. Therefore it is particularly useful to repeat step (c) 2 to 10, preferably 3 to 5 times, and to combine the organic phases thus obtained to give extract E3. In the course of the repetition of step (c) it is not necessary to change the ratio of the solvents (a) and (b) or the temperature. Due to the fact that during the cascade of repetitions the amount of the steroidal glycosides in the aqueous phase is reduced, the polarity changes by itself and allows the extraction of the more polar steroidal glycosides. By means of this operation it is ensured that substantially all steroidal glycosides present in extract E2 are transferred into extract E3.

Step d—Purification

Once extract E3 has been obtained by optionally combining all organic phases from step (c), the product is subjected to a further purification. Preferably, the extract is washed with water or an aqueous alkaline base, and the organic phase thus obtained is subjected to concentration and drying to give the final product.

Removal of Heavy Metals and PAH

Depending on the origin of the plant materials, they may contain traces of heavy metals like copper or zinc and PAH (polyaromatic hydrocarbons) which may be enriched during the process. In particular it is known that cultivated *Hoodia* may contain higher levels of metals because of the use of irrigation water which can cause build-up of salts and metals.

It has been discovered, as part of the present invention, that treating a *Hoodia* plant extract with absorption materials like e.g. activated charcoal, silica, kaolin, fullers earth and tonsil to adsorb PAH, and/or with chelating agents such as, e.g., EDTA or citric acid, to eliminate heavy metals by forming complexes preferably followed by a bleaching earth filtration step. The charcoal treatment is preferably conducted prior to the final drying of the product, while the chelating agents can be added to the wash water. This process of removing heavy metals and PAH constitutes a second aspect of the present invention. The process is useful in treating extracts obtained by any method, and is also a preferred step in the inventive process described above, for treating extract E3.

"Heavy metals" as used herein include but are not limited to arsenic, antimony, lead, bismuth, chromium, cadmium, iron, cobalt, copper, nickel, silver, mercury, titanium, zinc, tin, manganese.

The total heavy metal content in the extracts obtained according to the inventive process is generally below 200 ppm (parts per million), preferably below 100 ppm, most preferably below 50 ppm, and optimally less than 10 ppm.

In particular the level of specific individual heavy metals that affect the suitability of the extract for use in food (lead, cadmium, mercury, chromium and arsenic) is lowered via this process to levels generally below 5 ppm, preferably below 3 ppm and ideally below 1 ppm.

The heavy metal content in the inventive extracts is measured as follows:

A known weight of sample is digested in nitric acid using closed vessel microwave digestion. The digested sample is diluted in ultra pure water. Standards are prepared from commercial stock standard solutions. These, together with a blank are matched to the nitric acid content of the sample extract.

Metals, except mercury, are analysed using Inductively Coupled Plasma—Atomic Emission Spectrometry (ICP-AES). The standards and samples are introduced into the ICP-AES via a Cross Flow Gem Tip Nebuliser with a Scott-type spray chamber or, for arsenic, cadmium and lead, via an Ultrasonic Nebuliser (USN). The metal content of the samples is quantified by comparison of their emission intensity to that of the known standards at wavelengths characteristic to each element.

For mercury determination an aliquot of the sample extract and standards is spiked with hydrochloric acid to create favourable acid conditions. The standards and sample are reduced in a flow injection system (FIAS) using sodium borohydride, to form volatile ground-state mercury and this is swept into a cell in the Atomic Absorption Spectrometer (AAS). A lamp in the AAS is used to shine light of a suitable wavelength through the cell. The metal content of the samples is quantified by the comparison of their absorption of this light to that of the known standards.

The extracts obtained according to the inventive process are also low in polyaromatic hydrocarbons. Polyaromatic hydrocarbons include but are not limited to benzo(c)fluorine, cyclopenta(cd)pyrene, benz(a)anthracene, chrysene, 5-methyl chrysene, benzo(b)fluoranthene, benzo(j)fluoranthene, benzo(k)fluoranthene, benzo(a)pyrene, indeno(123,cd) pyrene, benzo(ghi)perylene, dibenz(ah)anthracene, dibenz (al)pyrene, dibenz(ae)pyrene, dibenz(ai)pyrene, dibenz(ah) pyrene. Benzo(a)pyrene is typically used as a marker for the total amount of these toxic PAH's.

The benzo(a)pyrene content in the extract obtained according to the inventive process is generally below 2 ppb (parts per billion), preferably less than 0.2 ppb.

For PAH's measurements, 1 g of extract is accurately weighed out and appropriate deuterium labelled internal standards are added (5 ng each of D8-naphthalene, D8-acenaphthene, D10-fluorene, D10-phenanthrene, D10-anthracene, D10-fluoranthene, D10-pyrene, D12-benz(a)anthracene, D12-chrysene, D12-benzo(b)fluoranthene, D12-benzo(k) fluoranthene, D12-benzo(a)pyrene, D12-indeno(123,cd) pyrene, D12-benzo(ghi)perylene, D14-dibenzo(ah)anthracene and D14-dibenz(ai)pyrene). The sample is wetted with ultra pure water (5 ml). Subsequently, dimethylformamide is added (50 ml) and the mixture is placed in an ultrasonic bath for 1 hour. Next, the extract is solvent exchanged to hexane (liquid-liquid extraction), saponified (reflux with methanolic potassium hydroxide for 3 hours) and further cleaned up using adsorption chromatography (deactivated silica gel). Finally, the extract is concentrated to approximately 100 µL, a suitable deuterated recovery standard is added (5 ng each of D8-acenaphthylene, D14-p-terphenyl and D12-benzo(e)pyrene), and analysed by gas chromatography using high resolution mass spectrometry detection. The quality of data is verified by the analysis of a reference material (Olive oil supplied by FAPAS (from FAPAS study T0618)) for which there are acceptable ranges of concentrations for Benz(a)anthracene, Benzo(b)fluoranthene, Benzo (a)pyrene, Indeno(123,cd)pyrene and Benzo(ghi)perylene. The measured concentrations of each of those compounds in the reference material must be within the defined limits. A reagent blank sample is also analysed.

Steroidal Glycosides

Steroidal glycoside compounds in the extracts obtainable by the inventive processes typically have the general formula (1):

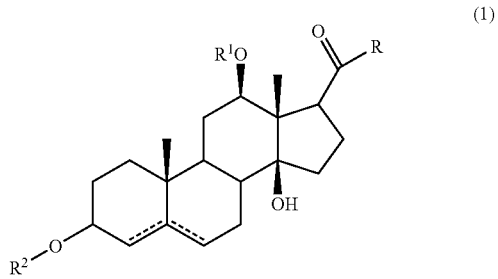

wherein

R=alkyl;

$R^1$=H, alkyl, tiglyol, benzoyl or any other organic ester group;

$R^2$=H or one or more 6-deoxy carbohydrates, or one or more 2,6-dideoxy carbohydrates, or glucose radical, or combinations thereof; and wherein the broken lines indicate the optional presence of a further bond between carbon atoms C4 and C5 or between carbon atoms C5 and C6.
Particularly preferred steroidal glycosides are analogs of Compound of Formula (1), including Compounds of Formula (2) through Formula (8), and mixtures thereof (Me=CH$_3$).
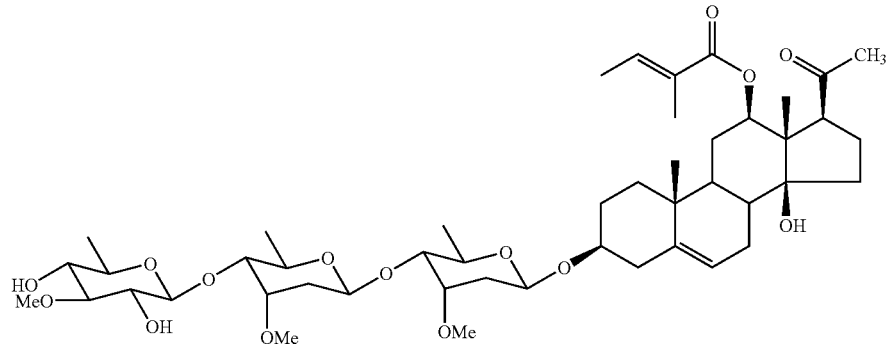
(2)
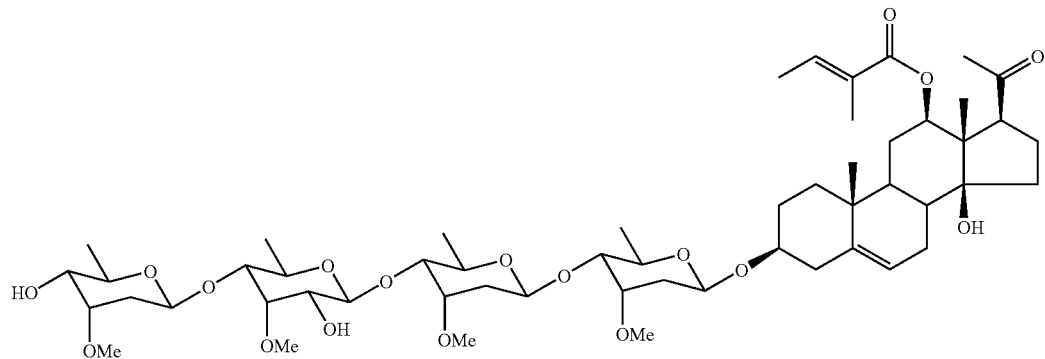
(3)
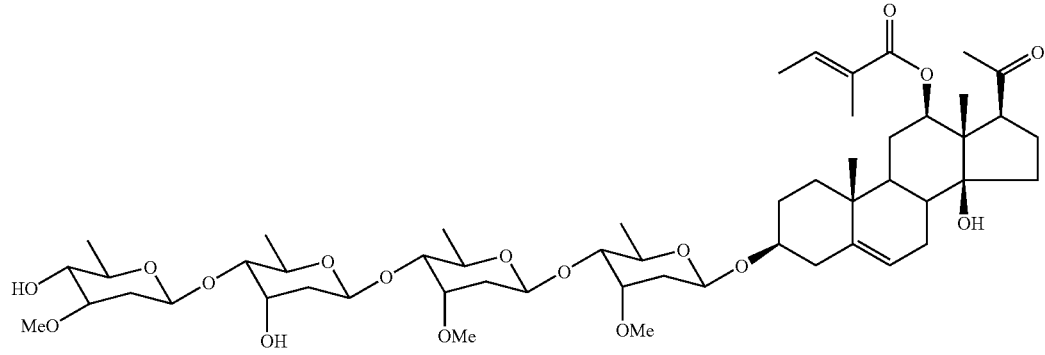
(4)
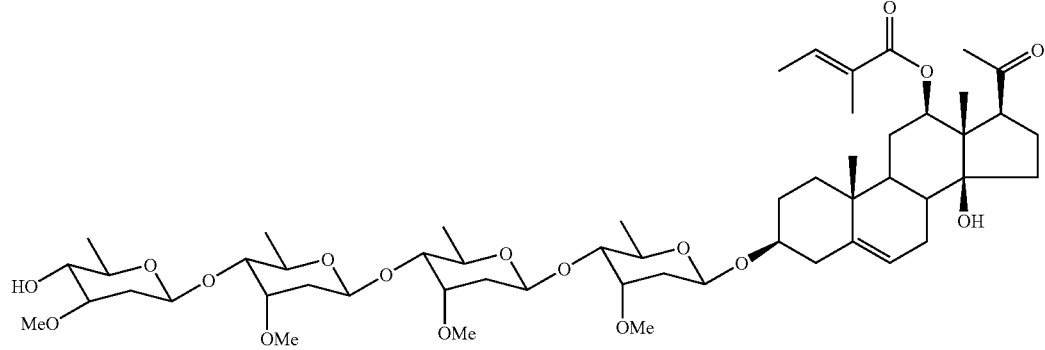
(5)

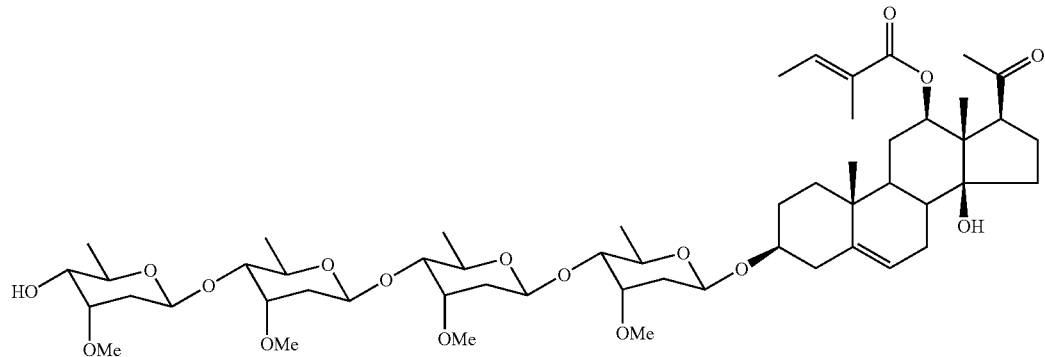

(6)

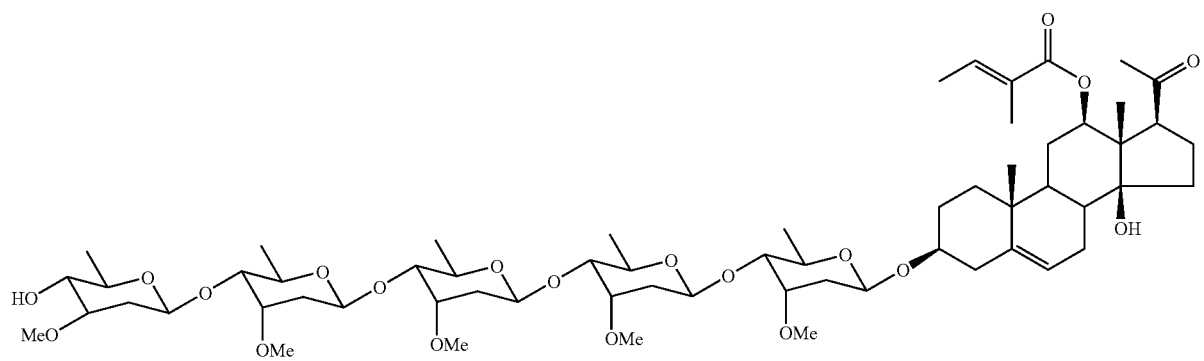

(7)

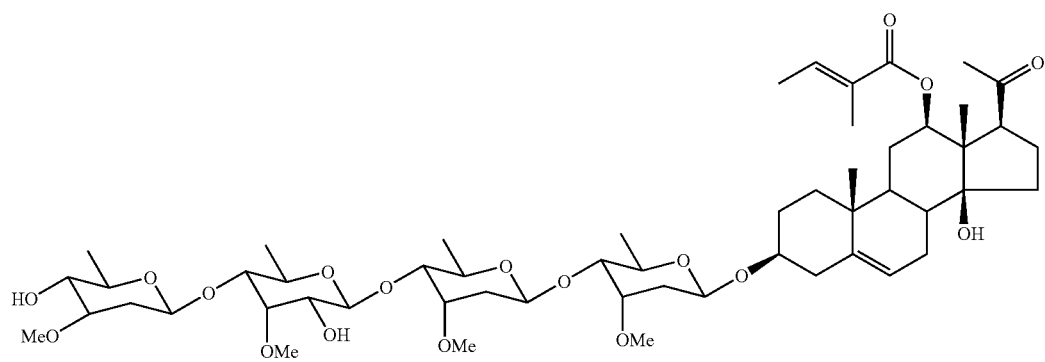

(8)

Other steroidal glycosides not specifically mentioned herein may be included in the inventive product. It will be understood that the invention also encompasses isomers, derivatives, salts, esters and analogs of the steroidal glycosides (preferably, biologically active appetite suppressants) and mixtures thereof.

The extract obtainable by the inventive process comprises at least 35%, preferably from 35 to 100%, more preferably from 60 to 100, most preferably from 70 to 100% steroidal glycosides based on the anhydrous extract.

The moisture content may be measured with any gravimetric method or Karl Fisher titration.

Steroidal glycoside concentrations are determined using high performance liquid chromatography (HPLC) with UV detection after extraction or dissolution. In case of dried plant material approximately 5 g of material is refluxed with approx. 80 ml of boiling methanol for 1 hr. The resulting extract is filtered and the solid material is washed with methanol. The combined filtrate and washing are transferred to a 100 ml flask and made to volume with methanol. 1 ml of the filtrate is evaporated to dryness and reconstituted in 1 ml acetonitrile/water (50/50 v/v). In case of extracts approximately 20 mg of the material is dissolved in 50 ml of methanol by sonication for 10 minutes. After filtration 1 ml of the filtrate is evaporated to dryness and reconstituted in 1 ml acetonitrile/water (50/50 v/v).

Steroidal glycosides are measured by LC-UV at 220 nm. To this end 20 μl of the extracts are injected onto a Zorbax RX-C8 analytical column of 250×4.6 mm packed with 5 μm particles and equipped with a Zorbax RX-C8 guard column of 12.5×4.6 mm packed with the same stationary phase. The column system is held at 40° C. Gradient elution is performed starting at 41.2% acetonitrile/methanol (85/15 v/v) and 58.8% water/methanol (85/15 v/v) at a flow rate of 1 ml/min. Initial conditions are held for 10 minutes before being linearly increased to 88.2% acetonitrile/methanol (85/15 v/v) and 11.8% water/methanol (85/15 v/v) over 30 minutes. After a final hold of 5 minutes the system is re-equilibrated to the starting conditions. Compound of Formula 2 of known purity (e.g. 95% in this case) is used for calibration. Compound 2 may be isolated from dried *Hoodia gordonii* using preparative liquid chromatography or may be synthesized (see e.g. U.S. Pat. No. 6,376,657, incorporated by reference herein). A stock solution at 100 μg/ml is prepared in acetonitrile/water (1/1 v/v) and further dilutions are prepared to yield additional calibration standards at 75, 50, 20, 10 and 5 μg/ml. UV response at 220 nm is used for quantification against the Compound 2 calibration line. Relative response factors based on molecular weight are used to quantify the steroidal glycosides against the Compound 2 calibration line. Steroidal glycosides are defined as all peaks eluting after 15 min that are not present in the blank acetonitrile/water (1/1 v/v) sample. For instance, compounds of Formula 2-8 together with their relative retention times and response factors, are summarized in Table 1.

TABLE 1

Relative retention times and response factors of some steroidal glycosides

| Compound | Relative retention time vs. Compound 2 | Response factor vs. Compound 2 |
|---|---|---|
| formula 2 | 1.000 | 1.000 |
| formula 8 | 1.066 | 1.164 |
| formula 3 | 1.128 | 1.164 |
| formula 4 | 1.191 | 1.130 |
| formula 5 | 1.292 | 1.146 |
| formula 6 | 1.328 | 1.146 |
| formula 7 | 1.399 | 1.309 |

The other steroidal glycosides' peaks eluting after 15 minutes have a response factor of 1.081 vs. Compound 2.

The extracts obtainable by the inventive process are particularly suitable for use in foods, especially in weight management products.

While the above summarizes the present invention, it will become apparent to those skilled in the art that modifications, variations and alterations may be made without deviating from the scope and spirit of the present invention as described and claimed herein. The invention will now be further illustrated in the following non-limiting examples.

Example 1

Preparation of a *Hoodia* Extract, Comprising 80% Steroidal Glycosides

Step a. In a 1 m$^3$ percolator, 25 kg of dried and milled *Hoodia* plants (average diameter less than 1.400 μm) with a steroidal content of about 0.9% by weight were placed and extracted at a temperature of about 50° C. over a period of 36 h by adding 200 kg of aqueous methanol (95% w/w). The extract was cooled down to about 20° C. and then filtered through a cellulose filter of 50 μm. Subsequently, the filtrate was concentrated using a standard evaporation equipment at 60° C. until the water content reached a value of about 30% by weight to give about 28 kg Extract E1 showing a dry matter content of about 6.5% by weight The liberated methanol was recycled for further extractions.

Step b. Extract E1 thus obtained was subjected to a liquid-liquid extraction by adding 3.75 kg n-heptane. The products were agitated over a period of about 5 minutes at about 50° C. After 30 minutes the phase separation was completed. The organic layer (about 4 kg) showing a dry matter content of about 3% by weight was separated and subjected to further purification steps in order to obtain chlorophylls, waxes and fatty acids. The aqueous phase A1 (about 28 kg) exhibiting a dry matter content of about 7% by weight was concentrated using a standard evaporation equipment at about 60° C. until the water content reached a value of about 55% by weight to give about 17 kg Extract E2 showing a dry matter content of about 12% by weight Step c. Extract E2 thus obtained was subjected to another liquid-liquid extraction by firstly adding a mixture of 1.25 kg n-heptane and 1.87 kg MEK, and then 2.5 kg water. The mixture was agitated over a period of about 15 minutes at about 40° C. After 20 minutes the phase separation was completed. Aqueous layer A2 (about 20 kg) showing a dry matter content of about 0.7% by weight was removed and subjected to further purification steps in order to obtain the short-chain active molecules. The organic layer, however, was subjected to another extraction with the same solvent/water mixture. In total, the extraction was conducted 4 times and subsequently all organic phases were combined to give about 7.7 kg of Extract E3 showing a dry matter content of 2.5% by weight Step d. Extract E3 thus obtained was washed with about 2 kg water comprising 0.1% by weight EDTA. Once again the organic phase was separated, filtrated over a bed of activated charcoal and dried at a temperature of about 60° C. until 0.16 kg of a final *Hoodia* extract were obtained, showing a dry matter content of more than 90% by weight and a content of steroidal glycosides of 81% by weight The extract had the following metal levels: Co<0.65 ppm, Cu 48.3 ppm, Zn 2.16 ppm, Mn<0.09 ppm, Ti<0.2 ppm, Ni<0.82 ppm, V<0.2 ppm, Cr<0.27 ppm, Fe 5.69 ppm The extract had a benzo(a)pyrene level of <0.2 ppb and a total PAH level of <0.2 ppb.

It will be apparent that for commercialization the previously mentioned process steps may be scaled up to the appropriate process and equipment sizes, types and standards practised in the particular or relevant food or agricultural industry.

It should be understood that the specific forms of the invention herein illustrated and described are intended to be representative only and that certain changes may be made therein without departing from the clear teachings of the disclosure.

The invention claimed is:

1. A process for production of *Hoodia* plants extract, the process comprising the steps of:
    (a) extracting the plants with aqueous $C_1$-$C_3$ aliphatic alcohols to provide a water-insoluble waste residue and a first aqueous extract E1;
    (b) subjecting extract E1 to a liquid-liquid extraction with lower paraffin hydrocarbons to provide an organic phase A1 and a second aqueous extract E2;
    (c) subjecting extract E2 to at least one liquid-liquid extraction with an aqueous mixture of lower paraffin hydrocarbons and lower dialkyl ketones to provide at least one aqueous phase A2 and at least one organic extract E3; and
    (d) drying extract E3 to a desired dry matter content to provide a final product.

2. Process according to claim 1, wherein the extraction in to step (a) is conducted with aqueous methanol.

3. Process according to claim 1 wherein the extraction in step (a) is conducted at a temperature of from 50 to 80° C.

4. Process according to claim 1 wherein the extract E1 of step (a) is subjected to filtration and concentration, so that the water content in the extract E1 is 20 to 40% by weight.

5. Process according to claim 1 wherein the extraction of step (b) is conducted with n-hexane or n-heptane.

6. Process according to claim 1 wherein the extraction of step (b) is conducted at a temperature of 20 to 70° C.

7. Process according claim 1 wherein the extract E2 of step (b) is subjected to concentration so that the water content in the extract E2 is 40 to 70% by weight.

8. Process according to claim 1 wherein the extraction of step (c) is conducted with an aqueous mixture of (a) n-hexane or n-heptane and (b) acetone or methylethyl ketone.

9. Process according to claim 8 wherein the extraction is conducted with an aqueous mixture comprising the organic solvents (a) and (b) in a weight ratio of 25:75 to 75:25.

10. Process according to claim 8 wherein the extraction is conducted with an aqueous solvent mixture having a water content sufficient to achieve a separation of the organic and the aqueous phase.

11. Process according to claim 1 wherein the extraction of step (c) is conducted at a temperature of 20 to 50° C.

12. Process according to claim 1 wherein the extraction of step (c) is repeated 1 to 10 times and the organic phases thus obtained are combined to give extract E3.

13. Process according to claim 1 wherein the process further comprises washing extract E3 with water or an aqueous alkaline base and concentrating the resulting organic phase.

14. Process according to claim 1 wherein the process further comprises treating extract E3 with an absorption material and/or a chelating agent.

15. Plant extract obtained by the process according to claim 1.

16. Food product comprising a plant extract obtained by the process according to claim 1.

* * * * *